United States Patent
Torre et al.

(10) Patent No.: US 9,376,693 B2
(45) Date of Patent: Jun. 28, 2016

(54) PRE-TREATED BIOMASS HAVING ENHANCED ENZYME ACCESSIBILITY

(75) Inventors: Paolo Torre, Arenzano (IT); Francesco Cherchi, Novi Ligure (IT); Piero Ottonello, Genoa (IT); Simone Ferrero, Tortona (IT)

(73) Assignee: Beta Renewables S.p.A., Tortona (AL) (IT)

( * ) Notice: Subject to any disclaimer, the term of this patent is extended or adjusted under 35 U.S.C. 154(b) by 463 days.

(21) Appl. No.: 13/817,859

(22) PCT Filed: Sep. 29, 2010

(86) PCT No.: PCT/IT2010/000410
§ 371 (c)(1),
(2), (4) Date: Aug. 9, 2013

(87) PCT Pub. No.: WO2012/042544
PCT Pub. Date: Apr. 5, 2012

(65) Prior Publication Data
US 2013/0313472 A1    Nov. 28, 2013

(51) Int. Cl.
| | | |
|---|---|---|
| *C12P 7/10* | (2006.01) | |
| *C08H 8/00* | (2010.01) | |
| *C08L 5/14* | (2006.01) | |
| *C08L 97/02* | (2006.01) | |

(52) U.S. Cl.
CPC ... *C12P 7/10* (2013.01); *C08H 8/00* (2013.01); *C08L 5/14* (2013.01); *C08L 97/02* (2013.01); *C12P 2201/00* (2013.01); *Y02E 50/16* (2013.01)

(58) Field of Classification Search
None
See application file for complete search history.

(56) References Cited

FOREIGN PATENT DOCUMENTS

WO    2009/108773 A2    9/2009
WO    2010/113129 A2    10/2010

*Primary Examiner* — Tanisha Diggs
(74) *Attorney, Agent, or Firm* — Edwin A. Sisson, Attorney at Law, LLC; Jeffrey J. Banyas

(57) ABSTRACT

This invention is to a biomass composition of 5 and 6 carbon sugars, lignin, and cellulose which has been steam exploded and the composition has a very high enzyme accessibility at 24 hours for hydrolysis.

17 Claims, No Drawings

PRE-TREATED BIOMASS HAVING ENHANCED ENZYME ACCESSIBILITY

PRIORITY AND CROSS REFERENCES

This patent application claims the priority from PCT/IT2010/000410 filed on 29 Sep. 2010 the teachings of which are incorporated in their entirety.

FIELD OF INVENTION

This invention is to the use of biomass to be hydrolyzed in the production of energy.

BACKGROUND

The use of biomass in the second generation ethanol processes is known. A typical process will pre-treat the biomass with at least a steam explosion, hydrolyze the cellulose in the presence of enzymes and then ferment the resultant product to ethanol. A possible pre-treatment equipment setup with conceptual process steps is disclosed in WO 2009/108773. While WO 2009/108773 provides equipment, it provides no operational details for carrying out or treating the biomass.

The focus of past research has been to develop or select better enzymes to hydrolyze the cellulose so that the hydrolysis step can go faster. However, very little work or research has been done on treating the biomass in a manner so that it is more accessible to the enzymes. As it is known that the more accessible the material is before hydrolysis, the faster the hydrolysis reaction and less use of enzymes. There exists therefore, the need for a biomass feedstock which has higher enzyme accessibility than does previous forms of the biomass feedstock.

SUMMARY

Described in this specification is a composition of biomass comprising a solid, a liquid, an amount of C5 sugars based upon the amount of arabinan and xylan and the monomers, dimers, oligomers and polymers of arabinose and xylose in the liquid and solid of the composition, an amount of C6 sugars based upon the glucan content which includes the monomers, dimers, oligomers and polymers of glucan in the liquid and solid of the composition and furfural wherein the composition is further characterized as having a 24 hour enzyme accessibility of at least 30%.

It is further disclosed that the ratio of the amount of C5 sugars to the amount of C6 sugars is greater than 0.50 and the ratio of amount of the furfural to the amount of C5 sugars and C6 sugars added to together is greater than 0 and less than or equal to 0.0060.

It is further disclosed that the ratio of amount of the furfural to the amount of C5 sugars and C6 sugars added together is greater than 0 and less than or equal to 0.0050 or more preferably be greater than 0 and less than or equal to 0.0040; or even more preferably greater than 0 and less than or equal to 0.0030 or most preferably greater than 0 and less than or equal to 0.0016.

It is further disclosed that the amount of the solids in the composition are in the range of 11 to 99% by weight of the composition; or more preferably in the range of 14 to 99% by weight of the composition; or even more preferably in the range of 16 to 99% by weight of the composition, with the mostly preferred ranges of 19 to 99% by weight of the composition, 21 to 99% by weight of the composition, 24 to 99% by weight of the composition, 26 to 99% by weight of the composition, 29 to 99% by weight of the composition, 31 to 99% by weight of the composition, 36 to 99% by weight of the composition and 41 to 99% by weight of the composition.

DETAILED DESCRIPTION OF THE INVENTION

Plant biomass is a preferred feedstock for fermentation processes. Provided below are the preferred feedstocks for making the highly enzyme accessible stream.

Apart from starch, the three major constituents in plant biomass are cellulose, hemicellulose and lignin, which are commonly referred to by the generic term lignocellulose. Polysaccharide-containing biomasses as a generic term include both starch and lignocellulosic biomasses. Therefore, some types of feedstocks can be plant biomass, polysaccharide containing biomass, and lignocellulosic biomass.

If the biomass is a polysaccharide-containing biomass and it is lignocellulosic, a pre-treatment is often used to ensure that the structure of the lignocellulosic content is rendered more accessible to the enzymes, and at the same time the concentrations of harmful inhibitory by-products such as acetic acid, furfural and hydroxymethyl furfural remain substantially low.

Polysaccharide-containing biomasses according to the present invention include any material containing polymeric sugars e.g. in the form of starch as well as refined starch, cellulose and hemicellulose.

Relevant types of biomasses for hydrolysis and mixing according to the present invention may include biomasses derived from agricultural crops such as e.g.: starch e.g. starch containing grains and refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like with a similar dry matter content.

The ligno-cellulosic biomass feedstock is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass Leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchardgrass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indiangrass, bermudagrass and switchgrass.

One classification of the grass family recognizes twelve subfamilies: These are 1) Anomochlooideae, a small lineage of broad-leaved grasses that includes two genera (*Anomochloa, Streptochaeta*); 2) Pharoideae, a small lineage of grasses that includes three genera, including *Pharus* and *Leptaspis;* 3) Puelioideae a small lineage that includes the African genus *Puelia;* 4) Pooideae which includes wheat, barely, oats, brome-grass (*Bronnus*) and reed-grasses (*Calamagrostis*); 5) Bambusoideae which includes bamboo; 6) Ehrhartoideae, which includes rice, and wild rice; 7) Arundinoideae, which includes the giant reed and common reed; 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and blue-stem grasses; 11) Micrairoideae; 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses. Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Therefore a preferred lignocellulosic biomass is selected from the group consisting of the grasses. Alternatively phrased, the preferred lignocellulosic biomass is selected from the group consisting of the plants belonging to the Poaceae or Gramineae family.

If the polysaccharide-containing biomasses are lignocellulosic, the material may be cut into pieces where 20% (w/w) of the biomass preferably ranges within 26-70 mm, before pre-treatment. The pre-treated material has preferably a dry matter content above 20% before entering the process. Besides liberating the carbohydrates from the biomass, the pre-treatment process sterilizes and partly dissolves the biomass and at the same time washes out potassium chloride from the lignin fraction.

The biomass will contain some compounds which are hydrolysable into a water-soluble species obtainable from the hydrolysis of the biomass. For example, cellulose can be hydrolyzed into glucose, cellobiose, and higher glucose polymers and includes dimers and oliogmers. Cellulose is hydrolyzed into glucose by the carbohydrolytic cellulases. The prevalent understanding of the cellulolytic system divides the cellulases into three classes; exo-1,4-β-D-glucanases or cellobiohydrolases (CBH) (EC 3.2.1.91), which cleave off cellobiose units from the ends of cellulose chains; endo-1,4-β-D-glucanases (EG) (EC 3.2.1.4), which hydrolyse internal β-1,4-glucosidic bonds randomly in the cellulose chain; 1,4-β-D-glucosidase (EC 3.2.1.21), which hydrolyses cellobiose to glucose and also cleaves off glucose units from cellooligosaccharides. Therefore, if the biomass contains cellulose, then glucose is a water soluble hydrolyzed species obtainable from the hydrolysis of the biomass.

By similar analysis, the hydrolysis products of hemicellulose are water soluble species obtainable from the hydrolysis of the biomass, assuming of course, that the biomass contains hemicellulose. Hemicellulose includes xylan, glucuronoxylan, arabinoxylan, glucomannan, and xyloglucan. The different sugars in hemicellulose are liberated by the hemicellulases. The hemicellulytic system is more complex than the cellulolytic system due to the heterologous nature of hemicellulose. The systems may involve among others, endo-1,4-β-D-xylanases (EC 3.2.1.8), which hydrolyse internal bonds in the xylan chain; 1,4-β-D-xylosidases (EC 3.2.1.37), which attack xylooligosaccharides from the non-reducing end and liberate xylose; endo-1,4-β-D-mannanases (EC 3.2.1.78), which cleave internal bonds; 1,4-β-D-mannosidases (EC 3.2.1.25), which cleave mannooligosaccharides to mannose. The side groups are removed by a number of enzymes; such as α-D-galactosidases (EC 3.2.1.22), α-L-arabinofuranosidases (EC 3.2.1.55), α-D-glucuronidases (EC 3.2.1.139), cinnamoyl esterases (EC 3.1.1.-), acetyl xylan esterases (EC 3.1.1.6) and feruloyl esterases (EC 3.1.1.73).

The composition of the accessible pre-treated biomass will comprise a liquid and a solid and can be characterized on the basis of its C5, C6, furfural amounts and enzyme accessibility.

The total C5's in the composition is the sum of arabinan and xylan in the composition which includes the monomers, dimers, oligomers and polymers of arabinose and xylose in the liquid and solid of the composition.

The total C6's in the composition is the glucan content which includes the monomers, dimers, oligomers and polymers of glucose in the liquid and solid.

As known in the literature, a typical steam exploded biomass will have a ratio of furfural to [C5's+C6's]×10000 of at least 50, with a ratio of C5's to C6's greater than 0.55. As shown in the experimental streams, the process described herein is capable of producing a steam exploded product with a furfural content greater than 0, that is always present, but having a ratio of furfural to (C5's+C6's)×10000 of less than 60. Therefore a composition having a ratio of C5's to C6's in the range of 0.45 to 0.54, and a ratio of furfural to [C5's+C6's]×10000 between 0 and 60, or more preferably 0 and 50, or more preferably 0 and 30 is contemplated.

Compositions from the steam explosion can be characterized as always having furfural and having the ratio of C5's to C6's less than 0.45 and a ratio of furfural to (C5's+C6's)×10000 of less than 40, or more preferably, a ratio of C5's to C6's less than 0.45 and a ratio of furfural to (C5's+C6's)×10000 of less than 15, or more preferably the ratio of C5's to C6's less than 0.45 and a ratio of furfural to (C5's+C6's)×10000 of less than 10; or more preferably a ratio of C5's to C6's less than 0.40 and a ratio of furfural to (C5's+C6's)×10000 of less than 40, or even more preferably a ratio of C5's to C6's less than 0.40 and a ratio of furfural to (C5's+C6's)×10000 of less than 9, the ratio of C5's to C6's less than 0.35 and a ratio of furfural to (C5's+C6's)×10000 of less than 10, or even more preferably, the ratio of C5's to C6's less than 0.30 and a ratio of furfural to (C5's+C6's)×10000 of less than 7.

The composition of the liquid portion of the stream is unique and can be described as always having furfural and having a ratio of C5's to C6's greater than 4.0 and a ratio of furfural to (C5's+C6's)×10000 of less than 80, or more preferably a ratio of C5's to C6's greater than 4.0 and a ratio of furfural to (C5's+C6's)×10000 of less than 60, or even more preferably a ratio of C5's to C6's greater than 4.0 and a ratio of furfural to (C5's+C6's)×10000 of less than 30, or the most broad range of a ratio of C5's to C6's greater than 3.0 and a ratio of furfural to (C5's+C6's)×10000 of less than 160.

The composition is further characterized by its enzyme accessibility. After pretreatment, of which the steam explosion is usually the last step, the biomass composition is sent to a hydrolysis step to reduce the viscosity by depolymerizing the cellulose. This is typically done in the presence of enzymes. The faster the reaction, the more accessible the cellulosic materials are to the enzymes, thus the term enzyme accessibility.

In the hydrolysis process, enzyme accessibility is the measure of how quickly a standard enzyme can hydrolyze the cellulosic components. The enzyme accessibility is expressed as a percent of the total amount of cellulose which is converted in a set amount of time.

In typical biomass compositions the enzyme accessibility is 90% at approximately 72 hours. This means that it took approximately 72 hours to hydrolyze 90% of the total available cellulosic material. A higher enzyme accessibility means that more cellulose materials are converted in a shorter amount of time. The enzyme accessibility can also be expressed as a percent at a unit of time. For example, an enzyme accessibility of 50% at 24 hours means that 50% of the available cellulose has been converted at 24 hours. This can also be expressed as 50% enzyme accessibility at 24 hours or a 24 hour enzyme accessibility of 50%.

The phrases enzyme accessibility of at least 30% at 24 hours, at least 30% enzyme accessibility at 24 hours, a 24 hour enzyme accessibility of at least 30% all mean that 30% to 100% of the cellulose has been converted at 24 hours.

It is unknown why the invented composition has such a high enzyme accessibility, but it is believed that the length of the steam explosion relative to the diameter of the valve creates the higher accessibility numbers.

As demonstrated in the experimental section, the enzyme accessibility of this material is such that by 24 hours at least 30% of the cellulose has been hydrolyzed. A preferred composition will have a 24 hour enzyme accessibility of at least 50%, with a more preferred composition having a 24 hour enzyme accessibility of at least 61%, with another preferred composition having a 24 hour enzyme accessibility of at least 71%, another preferred composition having a 24 hour enzyme accessibility of at least 75%, with another preferred composition having a 24 hour enzyme accessibility of at least 81%, with another preferred composition having a 24 hour enzyme accessibility of at least 91%; with the most preferred composition having a 24 hour enzyme accessibility of at least 90%. All 24 hour enzyme accessibility measurements are done using the enzyme amount equivalent to 30 FPU/g glucans.

The compositions were made in the following manner using equipment generally available from Andritz Inc., Glen Falls, N.Y., USA.

As detailed in the experimental section, the feed stock of the cellulosic biomass material used was that identified in the experimental table. Unless otherwise indicated, the feed stock was continuously fed to a first pressurized reactor. The cellulosic biomass feed stock was treated by adding steam at the rate of the indicated amount of steam at a pressure and temperature as indicated to dissolve and hydrolyze the hemi-cellulose, which is mainly C5s. The liquid stream comprised of dissolved hemi-cellulose, C5s and amorphous C6s and hydrolysis byproducts were extracted as a liquid from the pressurized reactor.

Examples of C5-sugar by-products that were removed as a liquor from the feed stock in the reactor include: aldehydes (HMF, furfural and formaldehyde), monomeric phenolics (vanillin and coniferylaldehyde) and acids (such as acetic acid and formic acid). After removal of the dissolved hemi-cellulose from the first reactor, the remaining feed stock was discharged from the first reactor to a sealing or extraction. The feed stock remained pressurized and was transferred from the first reactor via a discharge screw into a drain screw into an Andritz (MSD) Impressafiner®. The Impressafiner increased the pressure applied to the feed stock to a level above the pressure in the first reactor and to a level suitable for steam explosion and also removed more liquid as the pressure increased.

The steam explosion reactor was done as indicated to infuse the feed stock with water. After holding the feedstock at the indicated time, the feed stock was discharged from the steam explosion reactor through a 10 mm reducer followed by passing through a blow valve of 25 mm diameter into a blow line of 15 mm having a long of 5 m before being exposed to the atmosphere into a large collection vessel. The blow valve was opened the percentages indicated.

The discharge was done as follows—the pressure of the feed stock at the discharge of the steam explosion reactor was as indicated and dramatically reduced to atmospheric pressure by passing the feedstock through a blow-valve attached to the steam explosion reactor. The pressure drop across the blow-valve was the indicated drop in pressure. The conversion to steam of the water in the cells of the feed stock created a shredding explosion, of the cells in the cellulosic biomass feed stock.

The feed stock pressure at the discharge of the steam explosion reactor was as indicated and the pressure reduced to atmospheric pressure.

EXPERIMENTS

The aim of these experiments was to produce, by a physicochemical treatment ("pretreatment"), a material that could then be converted into bioethanol by enzymatic hydrolysis and fermentation. The material (in the following named "pretreated") has to meet various requirements. Thus, from the chemical point of view, it has to contain the largest possible amount of fermentable $C_5$ and $C_6$ sugars, calculated on the starting material (feedstock). From the physical point of view, the biomass has to be destructured in the pretreatment by destroying the intricate hemicellulose and lignin network which hampers the access of enzymes to the cellulose to be depolymerized.

The efficiency of the pretreatment is assessed on the basis of both these aspects. As regards the chemical effect, the data listed below show the typical parameters for the product obtained, namely the amount of $C_5$ and $C_6$ sugars in it and the amount of furfural, formed in it as the main degradation product.

By contrast, the physical effect is only assessed indirectly, namely by determining the "enzyme accessibility", i.e. how accessible the glucans present in the pretreated solid are to enzymes under standard conditions.

For comparison, the data listed below also include the corresponding parameters determined in some experiments conducted externally.

Apparatus Used

The pretreatment is carried out in two different types of apparatus, one operating batchwise and the other continuously.

The apparatus used for the batch method is an insulated reactor with a capacity of 10 dm³, which is connected to a 600-dm³ expansion vessel by a pipe that could be closed with the aid of a ball valve. The reactor has an inlet for the biomass at the top and with two steam inlets, also located at the top. The steam introduced into the reactor is regulated from a control panel, by means of a pneumatic actuator. The pressure of the steam is regulated by a manual valve but was kept low. The reactor is also equipped with a vent fitted with a butterfly valve. The latter is regulated with the aid of a tap operated manually. Finally, the reactor also had an inlet for compressed air, which is also regulated manually. On the other hand, the expansion vessel mentioned above is connected to the outside by a breather pipe and is fitted with a baffle located on its inside surface to direct the biomass coming from the reactor while maximizing the time of contact with the cooling jacket on the outside. The treated biomass is discharged through the outlet orifice at the bottom, which can be closed with a sliding gate valve. The equipment also includes a manual press, which can generate a pressure of 300 bar and which is used to remove the liquid phase from the solid after the pretreatment.

The apparatus used for the continuous method is essentially the same as that described in International Patent Application WO 2009/108773. The current version comprises a section for the introduction of the biomass through a pressure chamber, flanked by two ball valves. The biomass is fed from this chamber into a vertical reactor (Reactor 1), which is kept at the required pressure by introducing steam into it. After the treatment, the biomass is discharged with the aid of a screw conveyor located at the bottom of the reactor. This first screw conveyor is connected to a second, inclined screw conveyor, which is used to eliminate the liquid coming from the condensation of steam that may have been due to washing the material with water. Downstream of this section, the biomass is passed into a screw conveyor called "MSD Impressafiner" acquired from Andritz AG, which is operated at a high compression ratio. This device is used to form a material plug, needed to separate the upstream region from the one downstream, which may have been under a different pressure. In addition, a further removal of the liquid can also be effected here. The section lying downstream of the MSD Impressafiner comprises two worm conveyors, the first of which is called Reactor 2. The automatic discharge valve fitted at the end of these worm conveyors is connected to a pipe, called the "blow-down line", which creates an instantaneous decompression. The biomass is finally passed into a cyclone, where the volatile components and the excess steam are removed.

The liquids that had been removed are collected in two separate tanks, optionally kept under pressure for possible recycling.

The enzymatic hydrolysis itself has been carried out in 3.6-liter Infors laboratory-scale fermenters. These reactors are fitted with a jacket, and the temperature in them is regulated on the basis of the indication of a sensor fitted inside them. The pH is determined with the aid of a probe, which actuates two peristaltic pumps for the addition of an acid and a base, respectively. The bioreactors are fitted with rotary shaft stirrers connected to two Pelton turbines.

Materials Used

The experiments are carried out with two types of feedstock biomass, one from *Arundo donax*, and the other from fibre sorghum, whose compositions are as follows.

TABLE 1

Composition of the starting materials

|  |  | Sorghum | Arundo |
|---|---|---|---|
| Dry-matter content: | % | 83.00% | 92.00% |
| Water | wt-% | 17.00% | 8.00% |
| Glucans | wt-% | 26.97% | 33.34% |
| Xylans | wt-% | 14.42% | 19.17% |
| Acetyl groups | wt-% | 2.06% | 3.59% |
| Extractives | wt-% | 16.40% | 7.95% |
| Klason lignin | wt-% | 13.49% | 19.27% |
| Residues (after treatment at 575° C.) | wt-% | 5.30% | 5.86% |
| Other non-solubilized substances | wt-% | 4.35% | 2.82% |
| Total | wt-% | 100.00% | 100.00% |

The composition of the biomass has been determined by the following standard analytical methods.

Determination of Structural Carbohydrates and Lignin in the Biomass

Laboratory Analytical Procedure (LAP), released on 25 Apr. 2008

See *Technical Report* NREL/TP-510-42618, revised in April 2008

[NREL=National Renewable Energy Laboratory]

Determination of the Extractives in the Biomass

Laboratory Analytical Procedure (LAP), released on 17 Jul. 2005

See *Technical Report* NREL/TP-510-42619 of January 2008

Preparation of the Samples for the Determination of the Composition

Laboratory Analytical Procedure (LAP), released on 28 Sep. 2005

See *Technical Report* NREL/TP-510-42620 of January 2008

Determination of the Total Solids in the Biomass and the Total Dissolved Solids in the Liquid Samples Obtained Laboratory Analytical Procedure (LAP), released on 31 Mar. 2008

See *Technical Report* NREL/TP-510-42621, revised in March 2008

Determination of the Ash Content of the Biomass

Laboratory Analytical Procedure (LAP), released on 17 Jul. 2005

See *Technical Report* NREL/TP-510-42622 of January 2008

Determination of Sugars, By-Products and Degradation Products in the Liquid Phase Obtained
Laboratory Analytical Procedure (LAP), released on 8 Dec. 2006
See *Technical Report* NREL/TP-510-42623 of January 2008
Determination of the Insoluble Solids in the Pretreated Biomass
Laboratory Analytical Procedure (LAP), released on 21 Mar. 2008
See *Technical Report* NREL/TP-510-42627 of March 2008.

The enzyme cocktail used to determine the accessibility of the biomass to enzymes during the enzymatic hydrolysis has the following composition in all the experiments.

| Component\ | Amount vol-% | Density g/ml | | Specific activity\ |
|---|---|---|---|---|
| Cellulase complex | 87.4% | 1.08 | 100 | $FPU/g_{component}$ |
| Xylanase | 5.3% | 1.2 | 500 | $FXU/g_{component}$ |
| Hemicellulase | 6.6% | 1.1 | 470 | $FXU/g_{component}$ |
| Enzyme complex | 0.7% | 1.2 | 100 | $FBG/g_{component}$ |
| Total | 100.0% | 1.09 | | |

The cellulase complex is an enzymatic preparation that catalyses the decomposition of cellulose into glucose, cellobiose and glucose oligomers with a higher molecular weight.

The xylanase and hemicellulase solutions mainly catalyse the depolymerization of hemicellulose into its constituents in the form of simple or oligomeric sugars, but they also have some other catalytic activities to a lesser extent.

The "enzyme complex" is an enzymatic solution that acts on various carbohydrates and improves the activity of the overall solution prepared with it.

The enzyme cocktail has the following activity characteristics.

| Activity of the enzyme cocktail | | | |
|---|---|---|---|
| 94.39 | FPU/ml | 86.60 | FPU/g |
| 65.92 | FXU/ml | 60.48 | FXU/g |
| 0.84 | FBG/ml | 0.77 | FBG/g |

The various enzymatic activity units are defined as follows.

The filter paper unit (FPU) is determined and defined as described in the NREL's Laboratory Analytical Procedure (see Technical Report No. NREL/TP-510-42628 of January 2008). In this method, which involves the use of an industrial standard, the cellulase activity is determined in filter paper units (FPUs) per milliliter of the original (undiluted) enzymatic solution. To obtain quantitative results, the enzyme preparations must be compared on the basis of a conversion which is both significant and identical. For a given enzyme, 1 FPU is the amount of enzyme that is needed to release 2.0 mg of reducing sugars (measured as glucose) from 50 mg of Whatman No. 1 filter paper (conversion: 4%) in 60 minutes at 50° C. It has been defined by the International Union of Pure and Applied Chemistry (IUPAC) as the intercept for calculating the value of FPU.

The xylanase activity is determined in terms of FXU in relation to a standard enzyme with a known activity. The result obtained by a spectrophotometric determination carried out on the supernatant liquid as described below is compared with the standard curve obtained for the reference sample.

For this determination, the xylanase samples are incubated with a substrate consisting of arabino-xylanes extracted from Remazol-stained wheat. The unconverted substrate is precipitated with ethanol. The intensity of the blue colour which the degradation products in the unprecipitated substrate imparted to the supernatant liquid is proportional to the xylanase activity, but the colour profile can vary from one enzyme to the next.

$$\text{Activity of the sample}(FXU/g) = \frac{W}{C \cdot F \cdot D}$$

where
C is the enzyme activity read off the standard curve in FXU/ml
F is the volume of the sample in ml
D is the subsequent dilution of the sample (e.g. second or third dilution), and
W is the weight of the sample in g.

One FBG unit is the amount of enzyme that releases an amount of glucose (or reducing carbohydrates) with a reducing capacity equivalent to 1 mol of glucose per minute in a standard procedure carried out by the Somogyi-Nelson method described below.

Standard Reaction Conditions:
The sample should be diluted to an activity of 0.02-10 FBG/ml
Substrate: 0.5% of beta-glucans
Temperature: 30° C.
pH: 5.0
Reaction time: 30 minutes
Fungal beta-glucanase reacts with beta-glucans, forming glucose or reducing carbohydrates.

The pH has been maintained at a value of about 5 with the aid of an automatic adjustment system using an aqueous 1 M solution of $H_2SO_4$ and an aqueous 1 M solution of NaOH for purposes of correction.

Procedure of the Test Method

A certain amount of dry biomass is first prepared and then treated with water at room temperature to adjust its moisture content to the required level. Under the conditions used, the water is absorbed by the biomass instead of being present in the free form.

Batch Process (Carried Out in Apparatus 1)

In this case, the pretreatment consists of two successive stages. In the first one, the reactor is charged with a certain amount of biomass while the steam inlet valve is kept closed. This amount is about 1.5 kg, calculated on a dry-matter basis. Steam is then passed into the reactor until the required temperature and pressure are reached to ensure saturation. When the set point has been reached, the system is kept under stationary conditions for a predetermined time t. The pressure is then slowly released, and the biomass is recovered. The solid and liquid phases formed are separated by compressing the biomass in a press operated at a pressure of 300 bar. The solid phase is used in the second stage of the process, for a new cycle of operation in the same reactor. This stage is carried out as before, except that in this case the pressure is not released slowly through the vent, but instantaneously by fully opening the "steam explosion valve". The material therefore expands in the tank, and the volatile components and excess water are vented. The material obtained in this pretreatment is then passed into a laboratory-scale bioreactor for enzymatic hydrolysis, which is carried out under the following conditions:

T=45° C.
Stirrer speed=300 rpm
pH=5
Dry-matter content=7.5 wt-%
T=24 h.

The amount of glucose liberated in the material is determined by the method described above, and the value obtained is used to calculate the yield with the aid of the following equation:

$$Y_{glucose,24h} = \frac{c_{glucose,24h} \cdot (1 - WIS)}{\rho_{liquid} \cdot w_{glucans,0h} \cdot 1.111} \quad \text{(Eq. 1)}$$

where
$Y_{glucose,\,24\,h}$ is the glucose yield after 24 hours, calculated on the total solubilizable amount;
$c_{glucose,\,24\,h}$ is the concentration of glucose in the liquid phase after 24 hours;
WIS is the amount of non-solubilized solids after 24 hours, calculated in wt-% on the total weight;
$\rho_{liquid}$ is the density of the liquid phase;
$w_{glucans,\,0\,h}$ is the weight of glucans at time t=0, calculated on the total weight; and
1.111 is a factor that takes account of the difference between the molecular weight of glucose (180 g/mol) and that of the glucans (162 g/mol).

Continuous Process (Carried Out in Apparatus 2)

In this case, the material is first passed into the pressure chamber in a semi-continuous manner, using the required feed rate. When the required pressure has been reached, the biomass is fed into Reactor 1. The residence time there depended on the previous buildup, and steam is optionally passed in to make up for any loss of heat. The material is then passed first into the discharge screw conveyor and then into the inclined screw conveyor, where the first portion of excess liquid is removed. The material is then passed into the MSD Impressafiner, where more liquid is removed from it by compressing it. From there the biomass is transferred into Reactor 2 through the material plug mentioned above. The required temperature and pressure can be obtained in this reactor by passing steam into it, as necessary. The material is then transferred into the blow-down line by the last screw conveyor. The decompression taking place here brought the pressure down to the value prevailing in the cyclone. This blow-down line has a length of about 6 meters and an inside diameter of about 25 mm (1 inch).

The valve controlling this operation can be opened in different ways: notably it can be left open to a certain extent all the time, or it can be kept closed for a certain length of time and then opened to a certain extent for the next period.

The material obtained is then subjected to the same enzymatic hydrolysis and analysis as in the case of the batch method.

Experimental Conditions and Results

The continuous process is carried out 8 times, and the batch process twice, using the appropriate procedure described above in both cases. For comparison, the following table also includes the corresponding data for two other experiments, which were conducted in a plant that only comprised one steam explosion reactor, namely in an ENEA plant located at Trisaia.

The data listed in the following tables give the experimental conditions and the results obtained both for the composition of the biomass and for its accessibility to the enzymes used.

Table 2 shows the results obtained in all the experiments. Experiments 1-8 were carried out by the continuous process in Apparatus 2, and experiments 9 and 10 were carried out by the batch process, using Apparatus 1. Experiments 11 and 12 were conducted in the ENEA plant, comprising only one reactor with a screw conveyor and with a final explosion.

Table 3 shows the composition of the material obtained at the end of the pretreatment in terms of the amount of C6 and C5 sugars, calculated as dry matter, and furfural, together with the ratio between these components.

TABLE 2

Experimental conditions and the accessibility to enzymes achieved

| Expt. No. | Starting material Type | Composition (%) | | Method of pretreatment | Reactor 1 Pressure (bar) | Temperature (° C.) | Time (min) | Steam added (kg/kg dry) | Transfer (piston) Time (min) |
|---|---|---|---|---|---|---|---|---|---|
| 1 | Arundo Donax | Water | 8.00% | Continuous | 6 | 165 | 60 | 1.5 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |
| | | Klason lignin | 19.27% | | | | | | |
| | | Residues | 5.86% | | | | | | |
| | | Other insolubles | 2.82% | | | | | | |
| 2 | Arundo Donax | Water | 8.00% | Continuous | 6 | 165 | 60 | 1.5 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |
| | | Klason lignin | 19.27% | | | | | | |
| | | Residues | 5.86% | | | | | | |
| | | Other insolubles | 2.82% | | | | | | |
| 3 | Arundo Donax | Water | 8.00% | Continuous | 6 | 165 | 60 | 1.5 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |

TABLE 2-continued

Experimental conditions and the accessibility to enzymes achieved

| # | Material | Component | % | Mode | | | | | |
|---|---|---|---|---|---|---|---|---|---|
| | | Klason lignin | 19.27% | | | | | | |
| | | Residues | 5.86% | | | | | | |
| | | Other insolubles | 2.82% | | | | | | |
| 4 | Arundo Donax | Water | 8.00% | Continuous | 6 | 165 | 60 | 1.5 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |
| | | Klason lignin | 19.27% | | | | | | |
| | | Residues | 5.86% | | | | | | |
| | | Other insolubles | 2.82% | | | | | | |
| 5 | Arundo Donax | Water | 8.00% | Continuous | 6 | 165 | 60 | 1.7 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |
| | | Klason lignin | 19.27% | | | | | | |
| | | Residues | 5.86% | | | | | | |
| | | Other insolubles | 2.82% | | | | | | |
| 6 | Arundo Donax | Water | 8.00% | Continuous | 6 | 165 | 60 | 1.7 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |
| | | Klason lignin | 19.27% | | | | | | |
| | | Residues | 5.86% | | | | | | |
| | | Other insolubles | 2.82% | | | | | | |
| 7 | Arundo Donax | Water | 8.00% | Continuous | 9.8 | 180 | 20 | 1.6 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |
| | | Klason lignin | 19.27% | | | | | | |
| | | Residues | 5.86% | | | | | | |
| | | Other insolubles | 2.82% | | | | | | |
| 8 | Arundo Donax | Water | 8.00% | Continuous | 6 | 165 | 60 | 1.7 | 15 |
| | | Insoluble glucans | 33.34% | | | | | | |
| | | Insoluble xylans | 19.17% | | | | | | |
| | | Insoluble acetyls | 3.59% | | | | | | |
| | | Extractives | 7.95% | | | | | | |
| | | Klason lignin | 19.27% | | | | | | |
| | | Residues | 5.86% | | | | | | |
| | | Other insolubles | 2.82% | | | | | | |
| 9 | Fibre sorghum | Water | 17.00% | Batch | 9.8 | 180 | 20 | 2.3 | no |
| | | Insoluble glucans | 26.97% | | | | | | |
| | | Insoluble xylans | 14.42% | | | | | | |
| | | Insoluble acetyls | 2.06% | | | | | | |
| | | Extractives | 16.40% | | | | | | |
| | | Klason lignin | 13.49% | | | | | | |
| | | Residues | 5.30% | | | | | | |
| | | Other insolubles | 4.35% | | | | | | |
| 10 | Fibre sorghum | Water | 17.00% | Batch | 9.8 | 180 | 20 | 2.3 | no |
| | | Insoluble glucans | 26.97% | | | | | | |
| | | Insoluble xylans | 14.42% | | | | | | |
| | | Insoluble acetyls | 2.06% | | | | | | |
| | | Extractives | 16.40% | | | | | | |
| | | Klason lignin | 13.49% | | | | | | |
| | | Residues | 5.30% | | | | | | |
| | | Other insolubles | 4.35% | | | | | | |
| 11 | Arundo Donax | Water | 35.00% | Continuous | | | | | — |
| | | Insoluble glucans | 24.34% | | | | | | |
| | | Insoluble xylans | 12.53% | | | | | | |
| | | Insoluble acetyls | 3.76% | | | | | | |
| | | Extractives | 5.57% | | | | | | |
| | | Klason lignin | 13.28% | | | | | | |
| | | Residues | 4.10% | | | | | | |
| | | Other insolubles | 1.41% | | | | | | |
| 12 | Arundo Donax | Water | 35.00% | Continuous | | | | | — |
| | | Insoluble glucans | 24.34% | | | | | | |
| | | Insoluble xylans | 12.53% | | | | | | |
| | | Insoluble acetyls | 3.76% | | | | | | |
| | | Extractives | 5.57% | | | | | | |
| | | Klason lignin | 13.28% | | | | | | |
| | | Residues | 4.10% | | | | | | |
| | | Other insolubles | 1.41% | | | | | | |

TABLE 2-continued

Experimental conditions and the accessibility to enzymes achieved

| | Reactor 2 | | | | Explosion | | | Enzymatic hydrolysis at 24 h | |
|---|---|---|---|---|---|---|---|---|---|
| | | | | Steam | | | | Enzymes | Glucan yield |
| Expt. No. | Pressure (bar) | Temperature (° C.) | Time (min) | added (kg/kg dry) | Initial pressure (bar) | Final pressure (bar) | Valve opening (%) | added (FPU/g glucans) | (% of all possible soluble glucans) (%) |
| 1 | 13.5 | 195 | 8 | 5 | 13.5 | 1 | 75 | 10 | 57% |
| 2 | 13.5 | 195 | 8 | 5 | 13.5 | 1 | 75 | 20 | 70% |
| 3 | 13.5 | 195 | 8 | 5 | 13.5 | 1 | 75 | 30 | 83% |
| 4 | 13.5 | 195 | 8 | 5 | 13.5 | 1 | 75 | 40 | 82% |
| 5 | 13.5 | 195 | 4 | 5.2 | 13.5 | 1 | 65 | 25 | 80% |
| 6 | 16.5 | 200 | 6 | 5.5 | 16.5 | 1 | 90 | 25 | 79% |
| 7 | 13.5 | 195 | 8 | 5.2 | 13.5 | 1 | 65 | 30 | 74% |
| 8 | 17.1 | 205 | 4 | 5.6 | 17.1 | 1 | 45 | 30 | 75% |
| 9 | 12.5 | 190 | 8 | 2.5 | 12.5 | 1 | 100 | 25 | 44% |
| 10 | 16.5 | 200 | 14 | 2.7 | 16.5 | 1 | 100 | 25 | 46% |
| 11 | 21 | 215 | 3 | 1.45 | | 1 | 100 | 25 | 58% |
| 12 | 16.5 | 200 | 6 | 1.1 | | 1 | 100 | 25 | 40% |

TABLE 3

Composition of the biomass after the steam-induced explosion

| | Composition of the material after the steam-induced explosion Expt. No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C5, % (wt/wt) on a dry-matter basis | 7.46% | 7.46% | 7.46% | 7.46% | 13.48% | 3.74% | 7.31% | 10.69% | 15.71% | 13.48% | 11.07% | 18.26% |
| C6, % (wt/wt) on a dry-matter basis | 41.28% | 41.28% | 41.28% | 41.28% | 45.12% | 44.61% | 50.87% | 49.05% | 49.47% | 50.53% | 36.86% | 37.98% |
| Furfural, % (wt/wt) on a dry-matter basis | 0.08% | 0.08% | 0.08% | 0.08% | 0.12% | 0.028% | 0.03% | 0.08% | 0.18% | 0.38% | 0.40% | 0.06% |
| C5/C6 ratio | 0.181 | 0.181 | 0.181 | 0.181 | 0.299 | 0.084 | 0.144 | 0.218 | 0.318 | 0.267 | 0.300 | 0.481 |
| Furfural/(C5 + C6) * 10^(4) | 16.46 | 16.46 | 16.46 | 16.46 | 20.47 | 5.74 | 4.77 | 12.78 | 28.04 | 59.44 | 83.37 | 10.91 |

We claim:

1. A composition of biomass comprising a solid and a liquid, wherein the solid and the liquid in the composition comprise an amount of C5's, an amount of C6's, and an amount of furfural, wherein the amount of C5's is a weight sum of arabinan and xylan including monomers, dimers, oligomers and polymers of arabinose and xylose in the liquid and solid of the composition, the amount of C6's is a glucan content by weight including monomers, dimers, oligomers and polymers of glucan in the liquid and solid of the composition; wherein the composition is prepared by a continuous process which comprises a pretreatment of a starting material to form the biomass, said pretreatment comprises a steam explosion reactor equipped with a blow-line and wherein the composition is further characterized as having a 24 hour enzyme accessibility of at least 88% using an enzyme amount equivalent to 30 FPU/g glucans.

2. The composition according to claim 1 wherein the ratio of the amount of C5's to the amount of C6's is greater than 0.50 and the ratio of amount of the furfural to the amount of C5's and C6's added to together is greater than 0 and less than or equal to 0.0060.

3. The composition according to claim 1, wherein the ratio of amount of the furfural to the amount of C5's and C6's added together is greater than 0 and less than or equal to 0.0050.

4. The composition of claim 1, wherein the ratio of amount of the furfural to the amount of C5's and C6's added together is greater than 0 and less than or equal to 0.0040.

5. The composition of claim 1, wherein the ratio of amount of the furfural to the amount of C5's and C6's added together is greater than 0 and less than or equal to 0.0030.

6. The composition of claim 1, wherein the ratio of amount of the furfural to the amount of C5's and C6's added together is greater than 0 and less than or equal to 0.0016.

7. The composition of claim 1, wherein the amount of the solids in the composition are in the range of 11 to 99% by weight of the composition.

8. The composition of claim 1, wherein the amount of the solids in the composition are in the range of 14 to 99% by weight of the composition.

9. The composition of claim 1, wherein the amount of the solids in the composition are in the range of 16 to 99% by weight of the composition.

10. The composition of claim 1, wherein the amount of the solids in the composition are in the range of 19 to 99% by weight of the composition.

11. The composition of claim 1, wherein the amount of the solids in the composition are in the range of 21 to 99% by weight of the composition.

12. The composition of claim 1, wherein the amount of the solids in the composition are in the range of 24 to 99% by weight of the composition.

13. The composition of claim 1, wherein the amount of the solids in the composition are in the range of 26 to 99% by weight of the composition.

14. The composition of claim 1, wherein the amount of the solids in the composition are in the range of 29 to 99% by weight of the composition.

15. The composition of claim 1, wherein the amount of the solids in the composition are in the range of 31 to 99% by weight of the composition.

16. The composition of claim 1, wherein the amount of the solids in the composition are in the range of 36 to 99% by weight of the composition.

17. The composition of claim 1, wherein the amount of the solids in the composition are in the range of 41 to 99% by weight of the composition.

* * * * *